United States Patent
Allan (10) Patent No.: US 8,465,340 B1
(45) Date of Patent: Jun. 18, 2013

(54) NEST FOR SOLITARY BEES

(75) Inventor: Matthew James Allan, Easteigh (GB)

(73) Assignee: Pacific Pollination, LLC, El Dorado, AR (US)

( * ) Notice: Subject to any disclaimer, the term of this patent is extended or adjusted under 35 U.S.C. 154(b) by 182 days.

(21) Appl. No.: 13/095,133

(22) Filed: Apr. 27, 2011

Related U.S. Application Data (60) Provisional application No. 61/329,667, filed on Apr. 30, 2010.

(51) Int. Cl.
*A01K 47/00* (2006.01)

(52) U.S. Cl.
USPC .................................................. 449/4; 449/26

(58) Field of Classification Search
USPC .............. 449/4, 3, 26, 50; 119/706; 206/379, 206/3, 443, 733, 734, 499, 503, 509
See application file for complete search history.

(56) References Cited

U.S. PATENT DOCUMENTS

| | | | | |
|---|---|---|---|---|
| 3,191,199 A | * | 6/1965 | Barnes, Jr. | 449/4 |
| 3,267,497 A | * | 8/1966 | Dority | 449/4 |
| 3,367,483 A | * | 2/1968 | Studen | 206/379 |
| 4,301,766 A | * | 11/1981 | Piccone | 119/482 |
| D265,139 S | * | 6/1982 | Salvato | D30/160 |
| 4,765,007 A | * | 8/1988 | McCarthy | 449/4 |
| D298,577 S | * | 11/1988 | Faxon | D30/108 |
| 4,793,490 A | * | 12/1988 | Evert | 206/497 |
| 5,372,535 A | * | 12/1994 | Mills | 449/4 |
| 5,403,226 A | * | 4/1995 | Trafford | 449/4 |
| 5,509,846 A | * | 4/1996 | Kueneman et al. | 449/11 |
| 5,591,063 A | * | 1/1997 | McCarthy | 449/4 |
| 5,618,220 A | * | 4/1997 | Mills | 449/4 |
| 6,364,738 B1 | * | 4/2002 | Kendell et al. | 449/29 |
| 7,086,924 B2 | * | 8/2006 | Mills | 449/4 |
| D666,780 S | * | 9/2012 | Novich et al. | D30/108 |

* cited by examiner

*Primary Examiner* — Rob Swiatek
*Assistant Examiner* — Kathleen Iwasaki
(74) *Attorney, Agent, or Firm* — James M. Duncan, Esq.; Klein DeNatale Goldner (57) ABSTRACT

A nest for solitary bees may be fashioned from a rectangular solid of either a solid matrix or a number of nest elements. Each side of the nest contains a multiplicity of apertures, where each aperture provides a nesting cavity for the bees. Each aperture has an open end and a closed end. If fashioned from individual nest elements, the orientation of the apertures may be adjusted as desired, such that each element may be stacked upon an adjacent element in one of four orientations, so that the cavities of one element may be at 0°, 90°, 180° or 270° relative to an adjacent element. If desired, the aperture density of each side may be adjusted as desired. The configuration of the nesting cavities of the present invention reduces congestion at nest entrances and provides shelter to the bees from predators and the environment.

20 Claims, 8 Drawing Sheets

NEST FOR SOLITARY BEES

CROSS-REFERENCE TO RELATED APPLICATIONS

U.S. Provisional Application No. 61/329,667 for this invention was filed on Apr. 30, 2010, for which application this inventor claims domestic priority.

BACKGROUND OF THE INVENTION

Nests for cavity-nesting bees are known in the pollination industry and in the fields of research, conservation and education. They are also used by gardeners and enthusiasts. Known nests provide axial openings into which the solitary bees may nest. The entrances to the known nests, which are commonly U-shaped or circular in cross-section, are all on a single side of the assembly. While this configuration has been generally accepted, the present inventor has discovered that this arrangement can result in congestion of the bees at the entrance to the nest openings. This congestion reduces the ability of bees to identify and navigate to their nests. It also increases the amount of time required for the bees to access the safety of the nest and thus creates a longer exposure to hazards, such as predators, pesticides, and harmful environmental conditions.

SUMMARY OF THE INVENTION

A nest for solitary bees comprises a rectangular solid comprising either a solid matrix or a number of nest elements, which are usually, but not necessarily, square. Each side of the nest contains a multiplicity of apertures, each with an open end and a closed end, where each aperture provides a nesting habitat for the bees. If fashioned from individual nest elements, the orientation of the apertures may be adjusted as desired, such that each element may be stacked upon an adjacent element in one of four orientations, so that the cavities of one element may be at 0°, 90°, 180° or 270° relative to an adjacent element. If desired, the aperture density of each side may be adjusted as desired.

The orientation of the apertures of embodiments of the present invention encourages bees to populate the nest more than with the known nests and allows the bees to reach the security of the interior of the nest more expeditiously than with the known nests. Two or more stacked nests may be supported within a housing unit in such a way that a passage is left between opposing faces of the stacked nests. The nest elements may be arranged so that some or all of the open ends of the cavities are within the passage between the stacked nests. This arrangement encourages bees to populate the different cavities of the nest, while also providing shelter from predators and the environment. In addition, reduction of congestion at open ends of cavities improves recognition by each nesting female bee of its selected nest cavity, which reduces or eliminates the aggressive behavior and possible injury which may occur when females dispute possession of cavities.

DETAILED DESCRIPTION OF THE EMBODIMENTS

The present inventor, having found that the known nests create congestion at the entrance to the cavities has conceived a nest which not only provides the nesting cavities known in the prior art, but where embodiments of the new nest reduce bee congestion at the entrance to the cavities, and some embodiments provide additional shelter apart from the cavities themselves. The current invention provides a stacking nest for solitary bees, which is particularly useful in, but not exclusively intended for, commercial pollination of fruit and seed crops.

Figure 1:
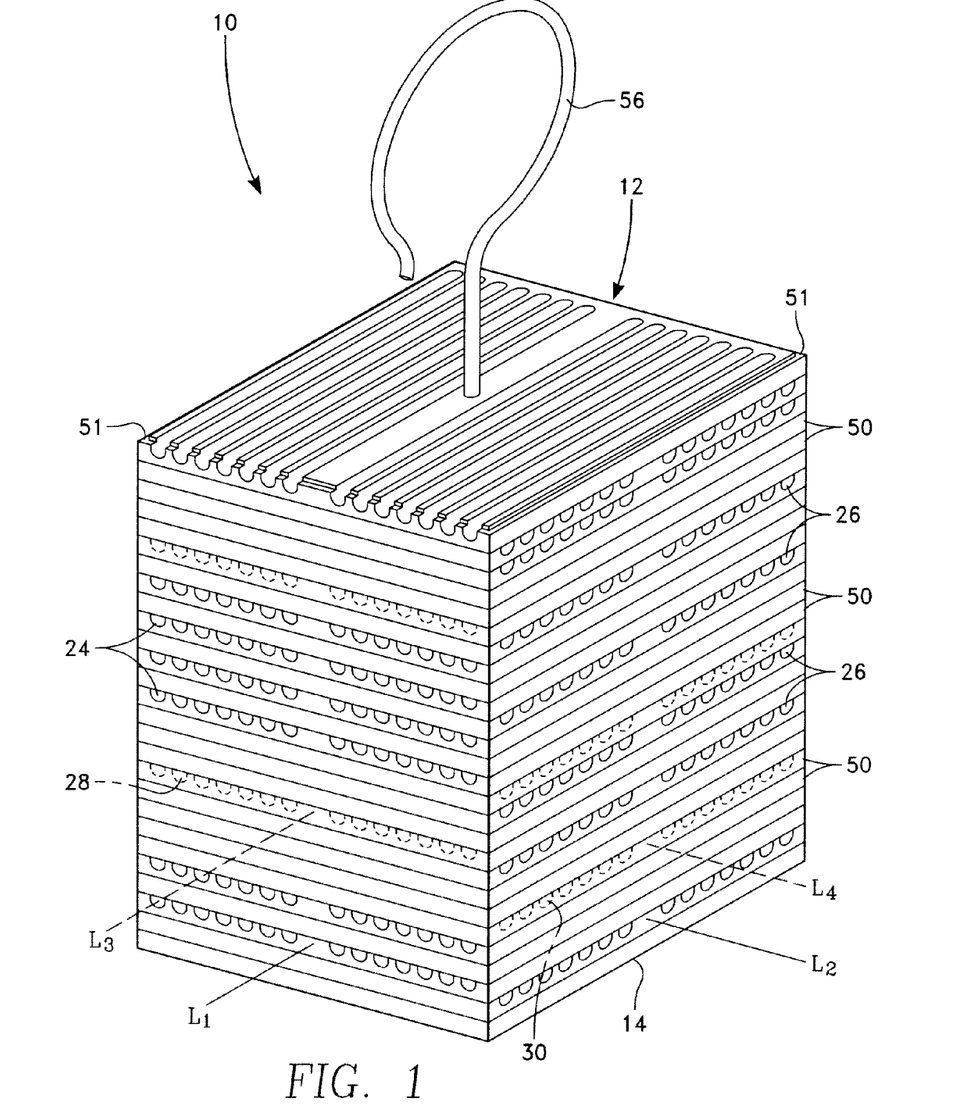
FIG. 1 is a perspective view of an embodiment of the nest according to the present invention, the nest having openings facing in four different directions.
Figure 1A:
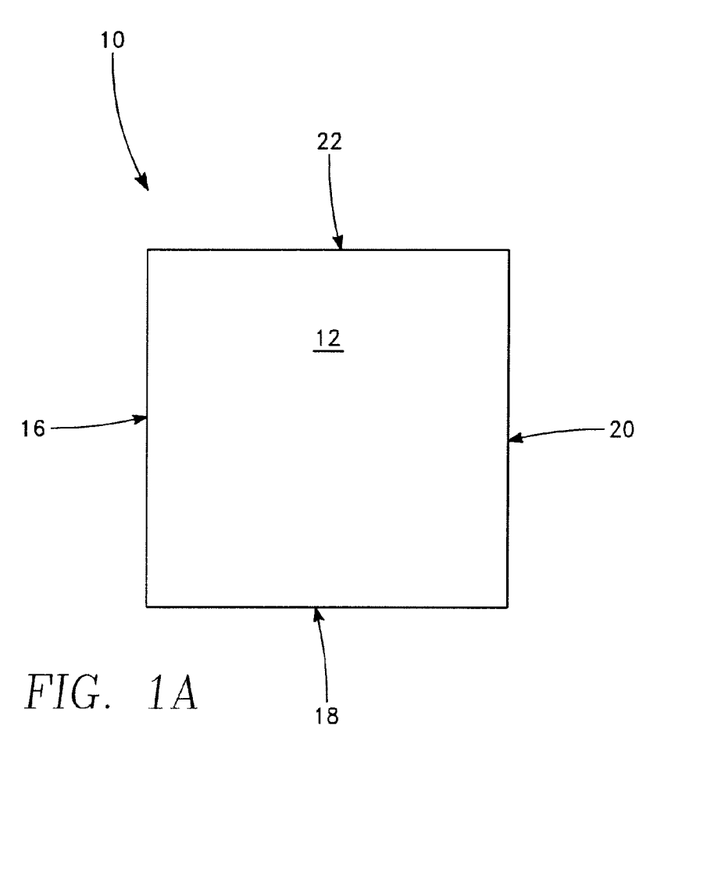
FIG. 1A shows a top view of the nest shown in FIG. 1.
Figure 2:
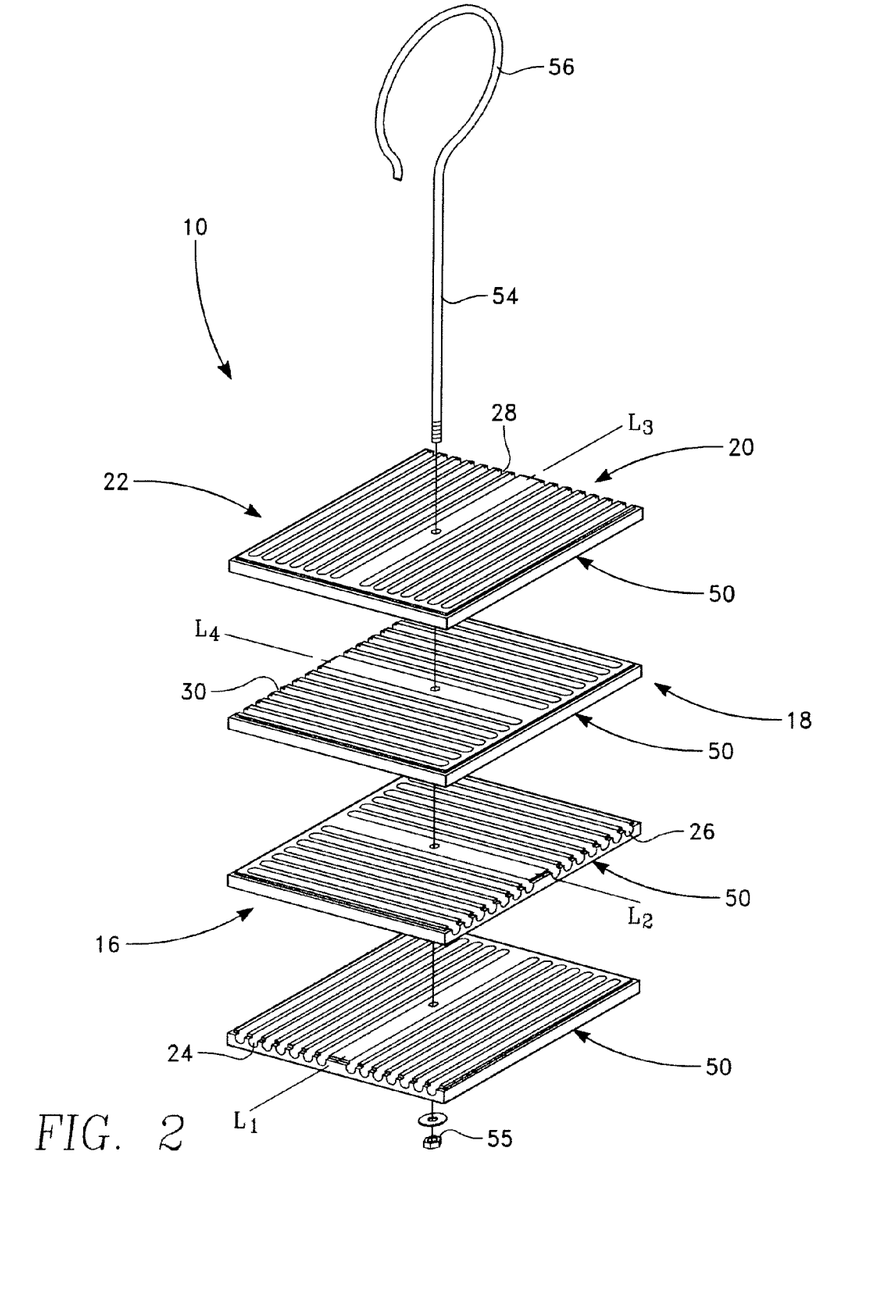
FIG. 2 shows an exploded view of the embodiment of FIG. 1.

Referring to FIG. 1 and FIG. 2, embodiments of the nest 10 comprise a rectangular solid. It is to be appreciated that the term "solid" does not refer to the composition of the matrix of the apparatus, which may comprise either a unitary solid or, as discussed below, a plurality of nesting elements, but rather the term is used in a geometric sense—the nest comprises a spatial solid. The nest 10 has a top 12, a bottom 14, a first side 16, a second side 18, a third side 20 and a fourth side 22. The first side 16 may be on the opposite side of the rectangular solid from the third side 20 and the second side 18 may be on the opposite side of the rectangular solid from the fourth side 22. The first side 16 has a large number of apertures 24 which extend from the first side to, but not penetrating, the third side 20. Each of the apertures 24 of the first side 16 has an axis $L_1$ which is normal to a plane defined by the first side. Likewise, second side 18 also has a large number of apertures 26 which extend from the second side to, but not penetrating, the fourth side 22, where each of these apertures has an axis $L_2$ normal to the second side. In the same fashion, the third side 20 comprises a large number of apertures 28, shown in hidden line, which extend from the third side to, but not penetrating, the first side 16, where each of these apertures 28 has an axis $L_3$ normal to the third side. Finally, the fourth side 22 comprises a large number of apertures 30 extending from the fourth side to, but not penetrating, the second side 18, where each of these apertures 30 has an axis $L_4$ normal to the fourth side. It is to be noted that for each of the axes $L_1$, $L_2$, $L_3$ and $L_4$, the axes do not coincide with or bisect any of the other axes. The nest 10 may be fabricated, by way of example, from drilling or machining the cavities in a solid block, or injection molding of a block having the aperture configuration described above.

Alternatively, an embodiment of nest 10 may comprise a stack of nest elements 50 which may be square in plan view, thereby enabling nest elements 50 to be stacked such that open ends of the apertures 24, 26, 28, 30 may face in any one of four directions. The density of nest entrances perceived by a nest-seeking bee is reduced to 25% of that which the bee would perceive if all open ends of the apertures were facing in the same direction. Each nest element 50 may engage with adjacent nest elements 50 by means of rebate 51 which is fashioned around the upper perimeter of each nest element 50 which engages in recess (not illustrated) in the underside of adjacent nest element. Alternative means of engagement may be utilized. In this and subsequent examples, the number of nest elements 50 in a stack may be varied dependent on the number of bees to be accommodated on a defined area of a specific crop. It is to be appreciated that the basis nest unit described above is utilized in the following described embodiments of the invention, whether the nest 10 comprises a solid structure or a plurality of nest elements 50.

Figure 3:
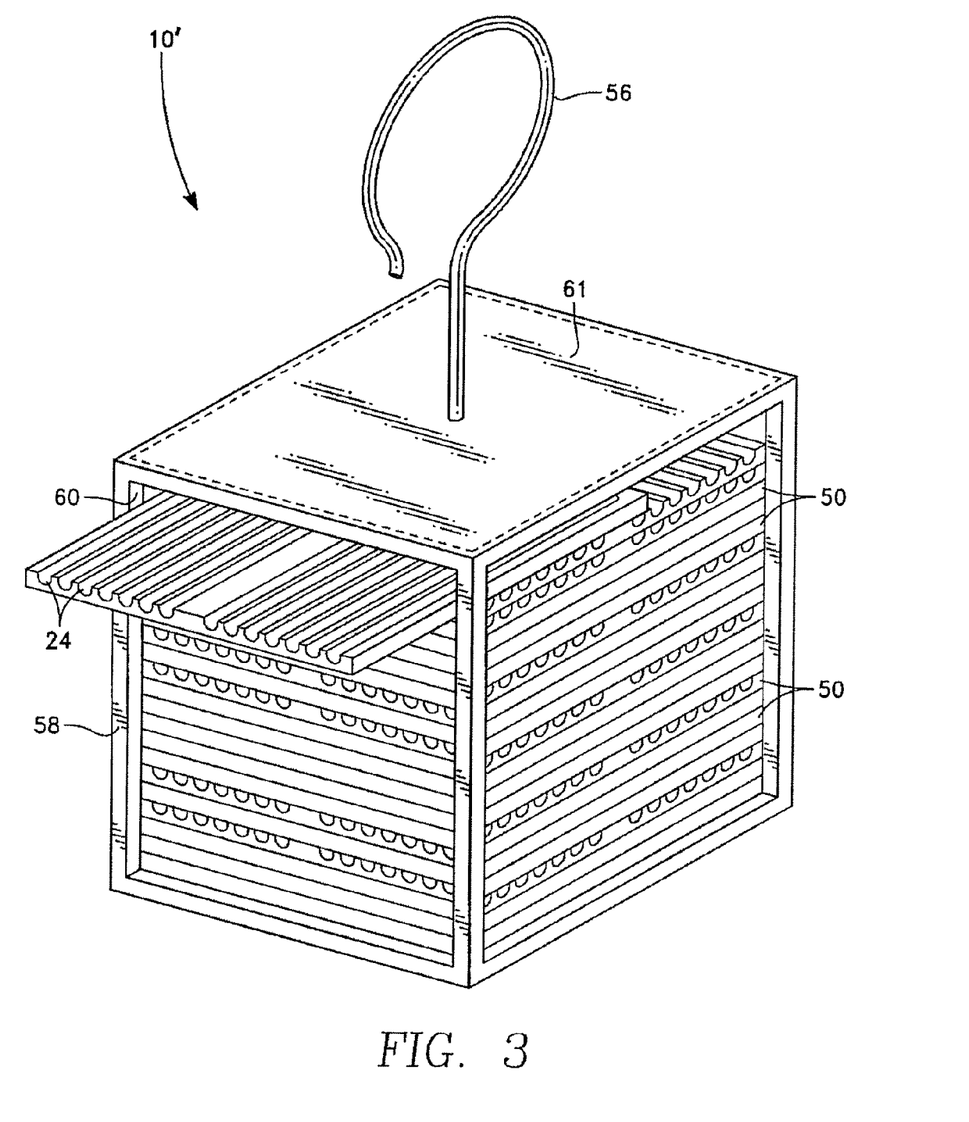
FIG. 3 shows an embodiment of the present invention in which stacked nesting elements are contained within a housing assembly.

Referring to FIG. 2, the components of a nest 10 fabricated from individual nest elements 50 are shown in the process of assembly. Nest 10 comprises a number of nest elements 50 stacked with open ends of apertures 24, 26, 28, 30 facing in four different directions, showing the orientation of axes $L_1$, $L_2$, $L_3$ and $L_4$. The stack of nest elements is supported by hanger 54 which passes through the centre of each nest element 50 and includes support 56 illustrated here as a hook, but which may alternatively comprise a carabiner clamp, cable tie, ring, string, flexible wire or other method of hanging or supporting nest 52 in a tree or from an agricultural structure. In FIG. 2 a nut or clamp 55 is shown as an example of a method of securing hanger 54. Other support mechanisms may be utilized. For example, FIG. 3 illustrates a stack of nest elements 50 supported in a housing 58. In this embodiment of the nest 10', nest elements 50 are inserted into housing 58 by passing them through an opening 60. Alternatively one part of housing 58 such as cover 61 may be removable to allow nest elements 50 to be located within housing 58, or housing 58 may be assembled around nest elements 50.

FIGS. 2 and 3 illustrate embodiments of a nest 10 comprising nest elements 50 with U-shaped apertures 24, 26, 28, 30 as described above, but the current invention is equally applicable for nests comprising apertures of different cross-section, whether formed by the engagement of corresponding grooves on upper and lower surfaces of adjacent elements, or by the engagement of a grooved surface with a planar surface, or by each aperture being fully contained within an individual nest element 50. The nest arrangement is also suitable for nest elements of any material and any method of manufacture. When fabricated from nest elements 50, the density of apertures 24, 26, 28, 30 for each of the four sides of the nest 10 is adjustable.

The dimensions of each nest element 50 may vary with the species of solitary bee it is intended for; preferred dimensions are 100 mm to 200 mm square, more preferably 125 to 160 mm square. The preferred diameter of circular cavities (or the mean diameter of non-circular cavities) is 6 mm to 10 mm, more preferably 8 mm to 9 mm.

It may be desirable to provide additional navigation cues to bees by applying different colors or patterns to nest elements 50, for example by using different colors of plastic in a molding process, or applying paint or other pigments to nest elements 50 and/or housing 58 during or after manufacture.

It may be advantageous to provide shade or protection to the open ends of apertures 24, 26, 28, 30. In addition to making the nests more attractive to bees in some circumstances, it provides protection against agrochemical sprays, particularly fungicides, which are commonly and in some cases repeatedly sprayed during bloom when the bees are active. A further advantage of providing shade or protection is that it prevents predatory animals, particularly birds, catching nesting female bees at their most vulnerable, i.e., when stationary or slow-moving at the entrance to their nests.

Figure 4:
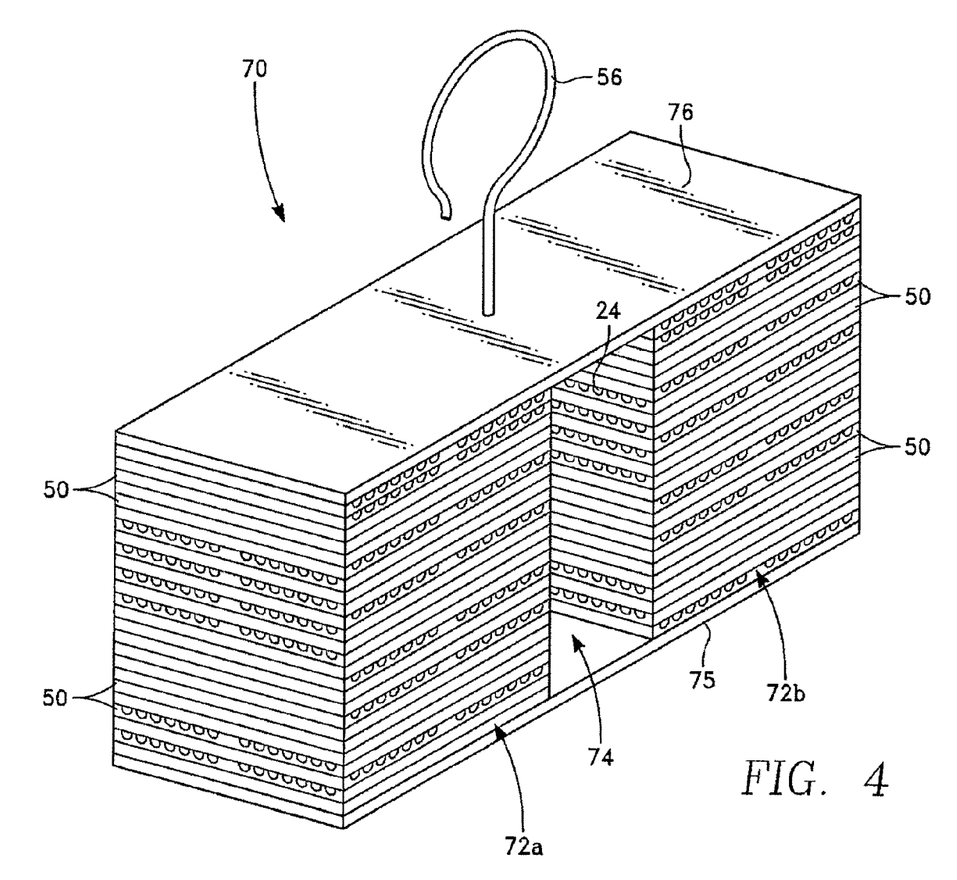
FIG. 4 shows an embodiment of the present invention which comprises two separate nest units contained within a housing assembly.

A further embodiment of the stacking nest for solitary bees is shown in FIG. 4; a nest 70 provides shade conditions for some or all of the open ends of apertures 24, 26, 28, 30. Two nest units 72a,72b, which may either be solid units as described above, or which may be nest units comprising nest elements 50, are held in alignment by base 75 and cover 76. Optional support 56 is provided for hanging nest 70 in a tree or agricultural structure. The passage 74 formed between stacks 72a,72b provides a protected and shady environment at the open ends of at least some of the apertures 24, 26, 28, 30. If desired, nest components 50 may be aligned and assembled so that all open ends of the apertures are within passage 74.

The preferred distance between opposing faces of stacks of nest elements 50 which form passage 74 is 25 mm to 100 mm, more preferably 50 mm to 75 mm.

Figure 5:
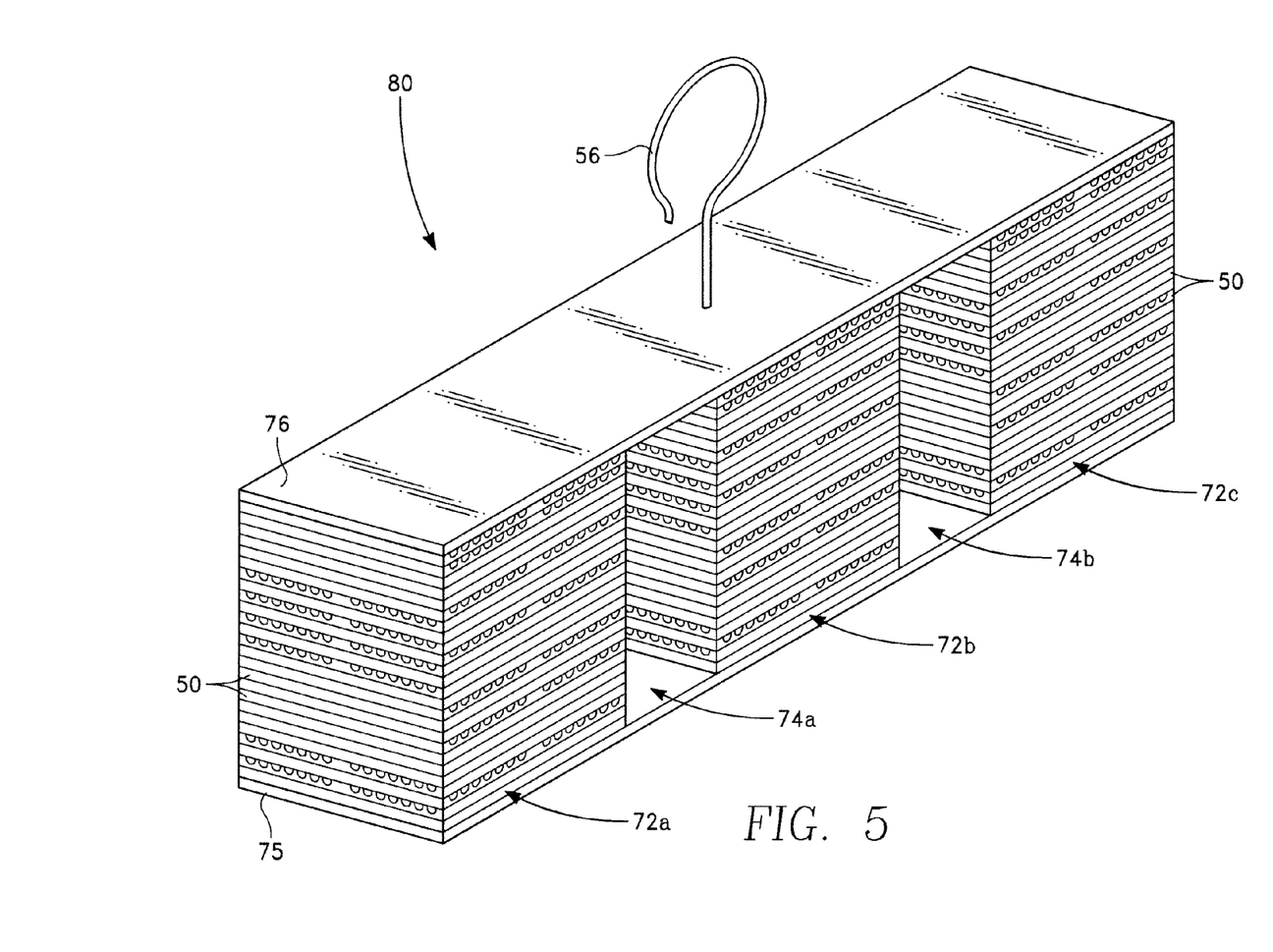
FIG. 5 shows an embodiment of the present invention which comprises three separate nest units contained within a housing assembly.

FIG. 5 shows an embodiment of a nest 80 in which three nest units 72a,72b,72c, which may be either solid units as described above, or which each comprise stacks of nest elements 50 are supported and held in alignment by base 75 and cover 76 in such a way that two passages 74a,74b are formed.

Figure 6:
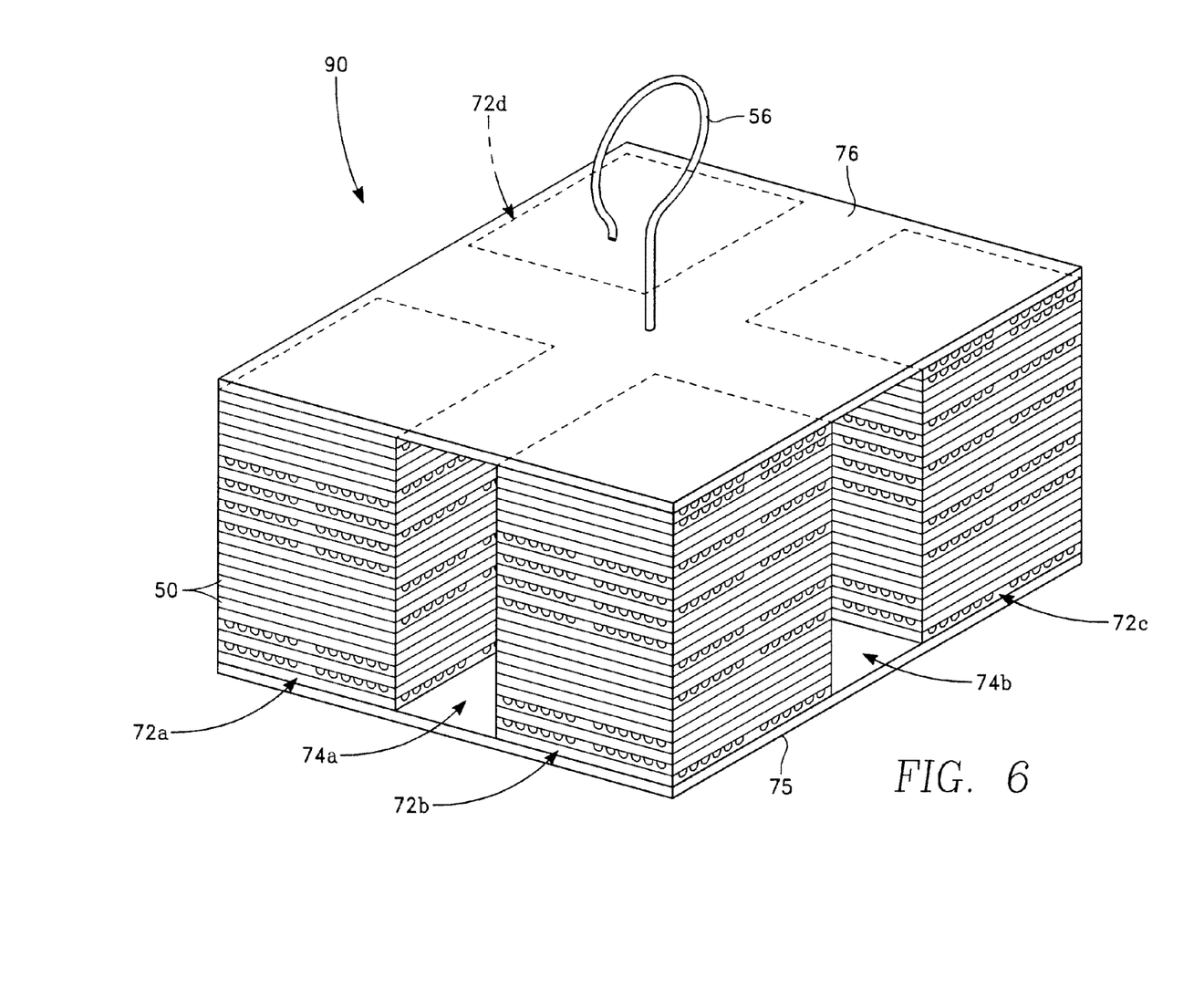
FIG. 6 shows an embodiment of the present invention which comprises four separate nest units contained within a housing assembly.
Figure 7:
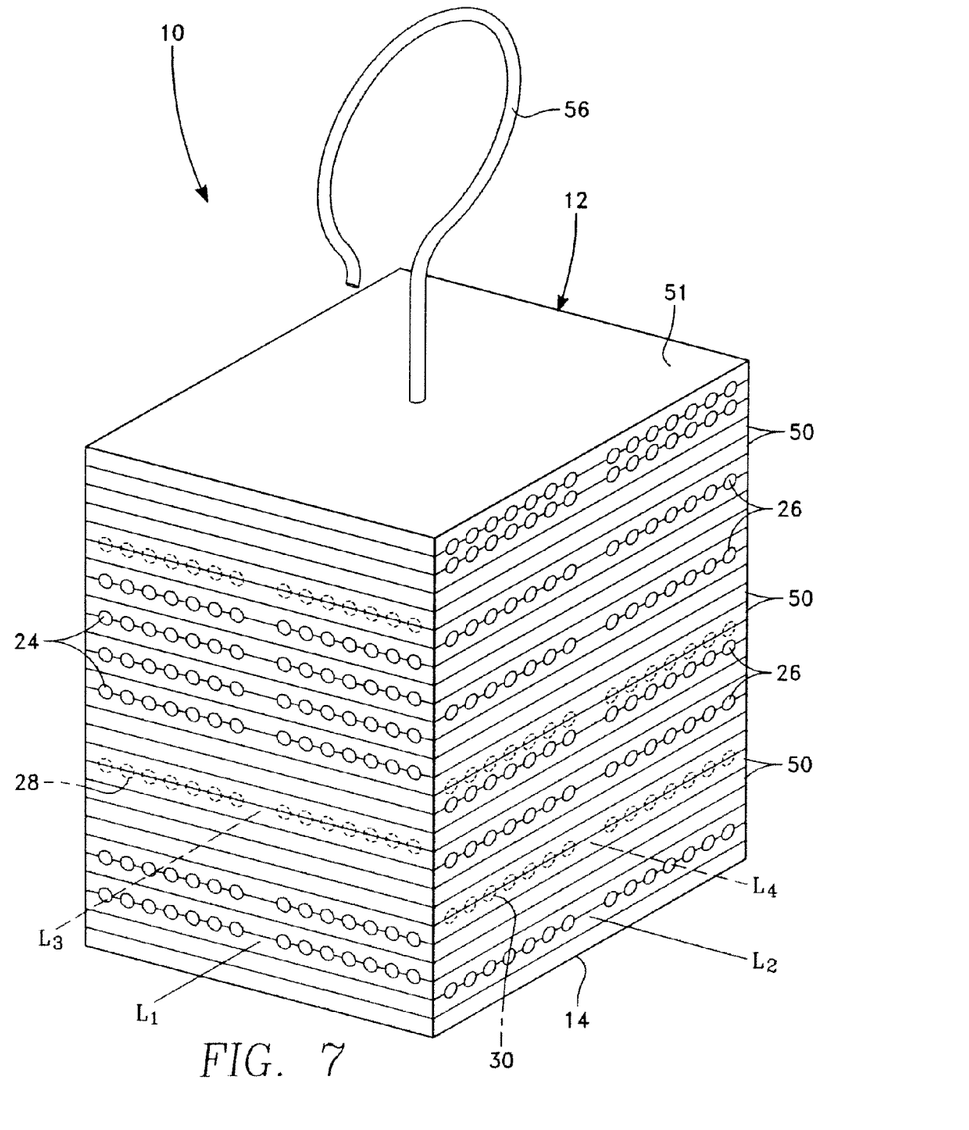
FIG. 7 shows an embodiment of the present invention in which each aperture is formed by opposite facing channels in adjacent nest elements in facing contact.

FIG. 6 shows a nest 90 comprising nest units 72a,72b,72c, 72d, which may be either solid units as described above, or which comprise stacks of nest elements 50. Referring to FIG. 6, base 75 and cover 76 support and hold in alignment solid nests or stacks 72a,72b,72c,72d of nest elements 50. Two intersecting protected and shaded passages 74a and 74b are formed. In this and in previous examples, the user may choose to stack nest elements 50 so that open ends of all apertures 24, 26, 28, 30 are within passages 74a, 74b, or alternatively at least some of the open ends of the apertures face outwards. Optional support 56 is provided for hanging nest assembly 70 in a tree or agricultural structure.

While the above is a description of various embodiments of the present invention, further modifications may be employed without departing from the spirit and scope of the present invention. Thus the scope of the invention should not be limited according to these factors, but according to the following appended claims.

What is claimed is:

1. A nest for solitary bees comprising:
   a rectangular solid comprising a top, a bottom, a first side, a second side, a third side and a fourth side, wherein the first side is on the opposite side of the rectangular solid from the third side and the second side is on the opposite side of the rectangular solid from the fourth side;
   wherein the first side comprises a first plurality of apertures extending as elongated passageways from the first side to, but not penetrating, the third side, each of the apertures of the first plurality having an axis normal to the first side;
   the second side comprises a second plurality of apertures extending as elongated passageways from the second side to, but not penetrating, the fourth side, each of the apertures of the second plurality having an axis normal to the second side;
   the third side comprises a third plurality of apertures extending as elongated passageways from the third side to, but not penetrating, the first side, each of the apertures of the third plurality having an axis normal to the third side;
   the fourth side comprises a fourth plurality of apertures extending as elongated passageways from the fourth side to, but not penetrating, the second side, each of the apertures of the fourth plurality having an axis normal to the fourth side; and wherein none of the axes of the apertures of the first, second, third and fourth pluralities coincide with or bisect any of the axes of the apertures of the other respective pluralities.

2. The nest of claim 1 wherein the first plurality of apertures are, with respect to the first side, configured in first vertical and first horizontal arrays, wherein the apertures in the first vertical array are in parallel alignment with one another and the apertures in the first horizontal array are in parallel alignment with one another.

3. The nest of claim 2 wherein the second plurality of apertures are, with respect to the second side, configured in second vertical and second horizontal arrays, wherein the apertures in the second vertical array are in parallel alignment with one another and the apertures in the second horizontal array are in parallel alignment with one another.

4. The nest of claim 3 wherein the third plurality of apertures are, with respect to the third side, configured in third vertical and third horizontal arrays, wherein the apertures in the third vertical array are in parallel alignment with one another and the apertures in the third horizontal array are in parallel alignment with one another.

5. The nest of claim 4 wherein the fourth plurality of apertures are, with respect to the fourth side, configured in fourth vertical and fourth horizontal arrays, wherein the apertures in the fourth vertical array are in parallel alignment with one another and the apertures in the fourth horizontal array are in parallel alignment with one another.

6. The nest of claim 1 wherein the rectangular solid comprises a plurality of square nest elements assembled in a vertically stacked arrangement.

7. The nest of claim 6 wherein the apertures are formed at opposite facing surfaces of vertically adjacent nest elements.

8. The nest of claim 7 wherein each aperture is formed by a channel in the facing surface of a first nest element in facing contact with a flat surface of a second nest element.

9. The nest of claim 7 wherein each aperture is formed by a channel in the facing surface of a first nest element in facing contact with an opposite facing channel of a second nest element.

10. The next of claim 6 wherein the nest elements comprise engagement means which align each nest element with adjacent nest elements.

11. The stacking nest of claim 6 wherein the nest elements comprise a plurality of colors.

12. The next of claim 6 wherein the nest elements are contained within a housing unit.

13. A nest for solitary bees comprising:
a rectangular solid comprising a top, a bottom, a first side, a second side, a third side and a fourth side, wherein the first side is on the opposite side of the rectangular solid from the third side and the second side is on the opposite side of the rectangular solid from the four side, wherein the rectangular solid comprises a plurality of square nest elements assembled in a vertically stacked arrangement;
wherein the first side comprises a first plurality of apertures extending from the first side to, but not penetrating, the third side, each of the apertures of the first plurality having an axis normal to the first side,
wherein the second side comprises a second plurality of apertures extending from the second side to, but not penetrating, the fourth side, each of the apertures of the second plurality having an axis normal to the second side;
wherein the third side comprising a third plurality of apertures extending from the third side to, but not penetrating, the first side, each of the apertures of the third plurality having an axis normal to the third side;
wherein the fourth side comprises a fourth plurality of plurality of apertures extending from the fourth side to, but not penetrating, the second side, each of the apertures of the fourth plurality having an axis normal to the fourth side; and
wherein none of the axes of the apertures of the first, second, third and fourth pluralities coincide with or bisect any of the axes of the apertures of the other respective pluralities.

14. The stacking nest of claim 13 wherein the apertures are formed at opposite facing surfaces of vertically adjacent nest elements.

15. The stacking nest of claim 14 wherein each aperture is formed by a channel in the facing surface of a first nest element in facing contact with a flat surface of a second nest element.

16. The stacking nest of claim 14 wherein each aperture is formed by a channel in the facing surface of a first nest element in facing contact with an opposite facing channel of a second nest element.

17. A nest for solitary bees comprising:
a first rectangular solid comprising a top, a bottom, a first side, a second side, a third side and a fourth side, wherein the first side is on the opposite side of the rectangular solid from the third side and the second side is on the opposite side of the rectangular solid from the four side;
wherein the first side comprises a first plurality of apertures extending from the first side to, but not penetrating, the third side, each of the apertures of the first plurality having an axis normal to the first side;
the second side comprises a second plurality of apertures extending from the second side to, but not penetrating, the fourth side, each of the apertures of the second plurality having an axis normal to the second side;
the third side comprises a third plurality of apertures extending from the third side to, but not penetrating, the first side, each of the apertures of the third plurality having an axis normal to third side;
the fourth side comprises a fourth plurality of plurality of apertures extending from the fourth side to, but not penetrating, the second side, each of the apertures of the fourth plurality having an axis normal to the fourth side;
wherein none of the axes of the apertures of the first, second, third and fourth pluralities coincide with or bisect any of the axes of the apertures of the other respective pluralities;
a second rectangular solid substantially the same as the first rectangular solid; and
a housing unit which maintains the first rectangular solid and the second rectangular solid in adjacent relationship, wherein a first interior passage is defined by a space between the first rectangular solid and the second rectangular solid.

18. The nest of claim 17 wherein the first rectangular solid and the second rectangular solid each comprise a plurality of square nest elements assembled in a vertically stacked arrangement.

19. The stacking nest of claim 17 comprising a third rectangular solid substantially the same as the first rectangular solid and the second rectangular solid, the third rectangular solid disposed within the housing unit such that the first rectangular solid, the second rectangular solid and the third rectangular solid are in linear alignment and a second interior passage is defined by the space between the second rectangular solid and the third rectangular solid.

20. The stacking nest of claim 17 comprising a third rectangular solid and a fourth rectangular solid each substantially the same as the first rectangular solid and the second rectangular solid, the third and fourth rectangular solids disposed within the housing unit such that the first rectangular solid and the second rectangular solid are in linear alignment, the first rectangular solid and the third rectangular solid are in linear alignment, the third rectangular solid and the fourth rectangular solid are in linear alignment, and the second rectangular solid and the fourth rectangular solid are in linear alignment, wherein intersecting interior passages are defined by spaces between the rectangular solids.

\* \* \* \* \*